United States Patent [19]

Mauldin

[11] Patent Number: 5,732,992
[45] Date of Patent: Mar. 31, 1998

[54] MEDICAL APPLIANCE TOOL PROVIDING ONE HAND ACTUATION

[75] Inventor: Cary M. Mauldin, Lake City, Fla.

[73] Assignee: Exactech, Incorporated, Gainesville, Fla.

[21] Appl. No.: 774,679

[22] Filed: Dec. 26, 1996

[51] Int. Cl.⁶ ................................................ A61B 17/92
[52] U.S. Cl. ............... 294/119.1; 606/99; 606/205; 81/163; 269/242; 269/6; 269/134; 269/135; 269/136
[58] Field of Search .............. 606/205, 99; 81/352, 81/387, 389, 155, 159, 163, 170, DIG. 4; 269/242, 6, 134, 135, 136; 294/119.1, 16

[56] References Cited

U.S. PATENT DOCUMENTS

| | | | |
|---|---|---|---|
| 577,255 | 2/1897 | Herstein | 81/163 |
| 1,047,046 | 12/1912 | Gronkowski | 81/163 |
| 1,665,511 | 4/1928 | Thomas | 81/163 |
| 1,886,907 | 11/1932 | Rugger | 81/163 |
| 5,417,693 | 5/1995 | Sowden et al. | 269/6 X |

*Primary Examiner*—Michael H. Thaler
*Attorney, Agent, or Firm*—Sven W. Hanson

[57] ABSTRACT

A tool is disclosed in which components can be grasped and secured using a single actuation motion. A mechanical system converts a single actuation motion into sequential motions at least in part mutually orthogonal. The advantages of this system are one-handed operation and ability to accommodate variations in dimensions of the components to be secured in the tool. A particular device is disclosed which is used in the handling of human prosthesis components during surgery.

13 Claims, 5 Drawing Sheets

MEDICAL APPLIANCE TOOL PROVIDING ONE HAND ACTUATION

BACKGROUND OF THE INVENTION

The invention relates to mechanical tools for grasping and retaining specific objects. More specifically, the invention pertains to tools for holding medical appliances in conjunction with their use in medical procedures. In particular, the present invention is a tool which allows a user, with one hand operation and a single actuation motion, to grasp, locate, and retain an appliance or component thereby capturing it on a handle in preparation for a medical procedure. The specific application in which this invention has been developed is in the introduction and removal of joint implants in the human body.

The procedure for applying a prosthetic implant such as a knee joint includes preparing the bone site by cutting and shaping to accommodate the prosthesis to be implanted. In what is often an iterative process, a trial piece is used as a guide to check the shape of the bone site to match the final prosthesis device. The trial piece is matched to the site, driven on, and fit and alignment checked with the mating limb implant. Selection of a resized trial piece may be required. Additional shaping is performed as needed. During this process, it is necessary to direct the trial piece to the site at the proper angle and orientation at which the final prosthesis device will be implanted and affixed. After the trial piece is properly fitted it must then be pulled off the limb. With the site properly prepared, the prosthesis device must then be directed in the same angle and orientation and driven in place. Various tools are currently available for holding the trial piece and prosthesis during these procedures. Typically with these existing tools, a jaw pair is closed by an actuator operating on a threaded shaft in a vise-like manner. After the jaws grip the component, a second actuator, again typically using a threaded rod and traveler, moves an impact base into contact with the component. An inherent feature of this type of device is the need to use two hands to effect the actuators. That is, while one hand grips the device handle, the second hand turns a wheel to operate the threaded traveler. In the surgical environment this operation is cumbersome and may require a second person's assistance. Because of the uncertain securing in the existing tools, prostheses are at times mistakenly driven onto a bone at an angle. Also, accommodating different sized components is difficult with the existing devices. Because the component is free while adjustment is made, the process of adjusting to a size change is awkward. In addition, when used for driving a prosthesis in place, most existing tools provide a load path which passes through threaded joints making for sloppy and unsure impaction.

What is desired is a device which can grasp and retain appliances such as prosthesis implants and trial pieces quickly and accurately while accommodating component differences in size and geometry. Such a device should allow for improved direction control and placement of the implants to the bone site and allow for accurate and sure impaction and removal. It is essential that such a device be operable with one hand to accommodate the surgical working environment.

The present invention provides a handled device which, with one hand and a single actuation motion, a user can grasp and securely retain prosthesis implants and trial pieces of varied sizes and geometries. In addition, the unique features of the present invention are easily applied to other situations where secure one-handed grasping of components by a tool is required.

SUMMARY OF THE INVENTION

It is an objective of the present invention to provide a tool which allows for manual grasping and retaining of components in a one-handed operation using a single actuation.

It is a further objective of the present invention to provide a tool which is capable of securely grasping a specifically designed prosthesis implant and providing a handle for accurately and repeatedly directing such an implant to a bone site.

It is another objective of the present invention to provide a tool for easily grasping prosthesis implants and presenting a direct and rigid load path to the implant from applied impacting devices.

It is yet another objective of the present invention to provide a system for mechanically grasping and then securing components such as prosthesis implants and other devices by applying a single actuation.

It is yet a further objective of the present invention to provide a tool for easily grasping, in a one-handed operation, prosthesis devices of varying geometries and sizes.

It is also an objective of the invention to provide a generally applicable mechanical system which transforms a single actuation motion into consecutive distinct motions for grasping and subsequently securing components against a rigid base.

The objectives of the present invention are satisfied by a device which utilizes a novel mechanical system which translates a single actuation motion into sequential motions at least in part orthogonal to each other. These sequential motions allow for the accurate grasping of a component in a manner to accommodate variations in dimensions prior to drawing the component to a secure position. Because these sequential motions are created by a single actuation motion, simple one-handed operation is made possible.

In a simplified configuration, the device consists of a handle, an impact base on which the particular component, such as a prosthesis, is to be secured, two jaws held on either side of the impact base, and a mechanism for drawing the two jaws together. The jaws have two arms, the first of which terminates above the impact base and is used to grasp the component. The second arm of each jaw is held adjacent to a slide surface formed on the impact base. This slide surface is, in most configurations, on the opposite side of the impact base from the surface on which the components are to be secured. A user grasps the handle of the tool, places a component on the impact base, and with the grasping hand operates an actuator such as a thumbwheel. The jaws are drawn together in a first motion until a jaw finger on each upper arm contacts the component. The jaws then begin to rotate about this point. The second arm of the jaws are dragged along the slide surface at a contact point as the jaws are further drawn together. Actuation continues. The rotation of the jaws results in the jaws being "levered" away from the impact base in a second motion by the second arm with the result that the finger, now grasping the component, is drawn to the impact base. Alternatives to the finger as a means of grasping the components are also provided. Variations in contour of the slide surface are also provided which create different motions for particular applications.

In the specific application of applying prosthesis implants, the handle is rigidly connected in line with the impact base. This is to provide a direct load path from the end of the handle which is typically struck, in use, with a mallet to drive on a prosthesis device. The end of the handle also contains a threaded connection for connecting a slap-hammer or similar device for removing implants. Preferably, the mechanism used to draw the jaws together is an elongated rod which is threaded into pivot posts which pivot inside a hole in each jaw. As the rod is turned, the jaws are drawn inward, by the pivot posts, on the rod threads. The actuator thumbwheel is connected to the elongated rod. A spring is provided to push the jaws into close proximity to the impact base. Alternative configurations are provided which employ the same unique mechanism including configurations with a single jaw piece, or with a resilient jaw piece which provides an internal pivot, or a configuration without a handle.

In order to better accommodate component differences in shape and dimension, an impact capture plate is provided secured to the impact base. This plate can be contoured or stepped to match the shape of the particular component, providing a more secure placement. This plate is best formed of plastic to help prevent damage to the components.

The claimed invention is a unique device for providing improved handling of prosthesis implants and similar components. The features of the device provide an ease of use unavailable in prior existing tools. The design of the tool is particularly suited for operating room conditions and provide quick and secure handling of prostheses. The following drawings and description below provides details of the preferred embodiments of the invention. Modifications and alternative configurations embodying the same novel principles will be obvious to one skilled in the art.

DESCRIPTION OF THE PREFERRED EMBODIMENTS

The functioning of the present invention revolves about a mechanical structure which translates a single actuation motion into two sequential substantially orthogonal motions. These orthogonal motions are then applied to first grasp and locate a component and, second, to draw the component to a base to secure it into position for handling.

Figure 1A:
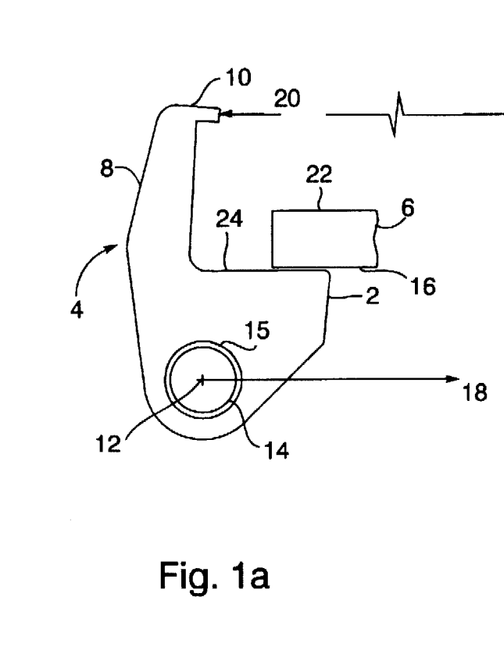
FIGS. 1a and 1ba consist of two views of the same jaw element of the invention depicting the sequence of motions of an exemplary mechanical system of the invention.

This structure is demonstrated by example in FIG. 1. A lever arm 2 of a jaw 4 is in slidable contact with an impact base 6 at a slide surface 16. A jaw arm 8 terminates at a finger 10 positioned generally adjacent an impact surface 22 of the impact base 6. The two arms extend at substantially different angles from a pivot axis 12 defined by the centerline axis of a pivot post hole 15. However, depending on the placement of the pivot axis in alternative configurations, the included angle between the jaw arm and lever arm may be very small or zero. A pivot post 14 is pivotably retained in the hole 15. The pivot axis 12 is generally perpendicular to the plane of the jaw 4. The pivot post is connected to a retraction means 18 (represented, for clarity, in this view by the resultant motion of the jaw) by which the jaw may be moved laterally substantially parallel to the impact base 6 slide surface 16.

Figure 1B:
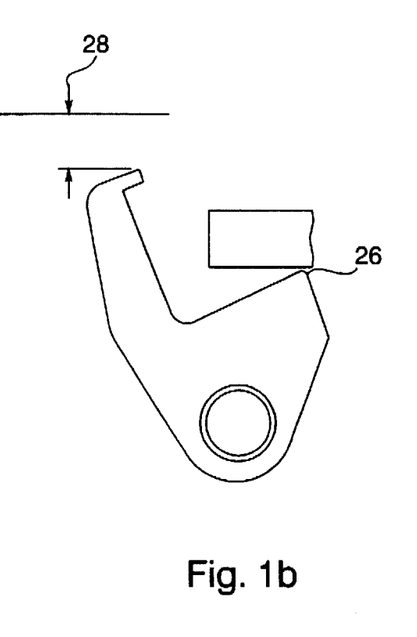

In operation, a component is placed against the impact surface 22 of the impact base. The jaw is moved laterally until the finger 10 comes into contact with, and is resisted by, the component 20 (represented functionally for clarity). During this lateral motion, the lever arm remains in contact and slides against the slide surface 16. The lever arm contacts the slide surface along a flat contact surface 24 in this configuration. After contact with the component, simple lateral motion of the jaw is restrained. Continued lateral motion of the pivot post 14 must come from rotation of the jaw about the finger/component contact. However, the lever arm cannot simply rotate about this point because of the impact base interference. The result of continued lateral motion induced by the retraction means is an orthogonal motion of the jaw as it is levered from the impact base by the lever arm (FIG. 1b). The finger is coincidentally drawn to the impact base, and with it the component. The relative displacement 28 of the finger is essentially orthogonal to the retracting motion as shown in FIG. 1ba. The component, of course, must have a shelf, lip or ledge or similar structure in which, or on which, the finger resides such that the component will be drawn down with the finger. Clearly, if the component is fairly rigid, very little rotation of the jaw is required to create significant force retaining the component to the impact base. Therefore, the rotations and displacements shown in FIG. 1ba are greatly exaggerated.

While this example has been made with a single jaw, it is preferable with a hand-held device to have multiple opposing jaws which will be drawn relatively together such that the component does not move laterally upon contact with the fingers. In this manner, the jaws are actually mutually resisting. To accomplish this, structures are provided in the below description to assure symmetry and simultaneous contact of the multiple jaws with the component to be grasped.

Figure 2:
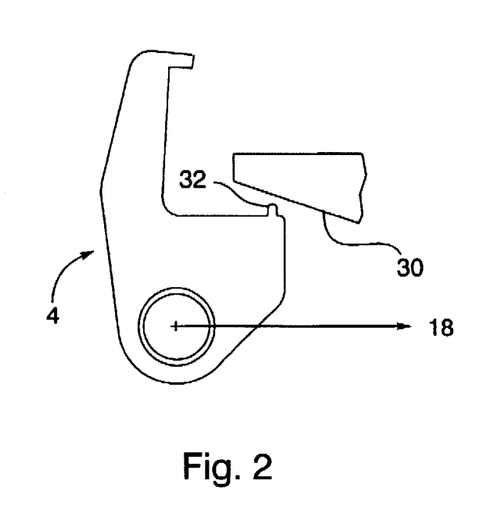
FIG. 2 depicts an alternative design of the jaw element of FIG. 1 in which the sliding surface is replaced with a contact point.

In an alternative configuration, the slide surface 16 and contact surface 24 are neither parallel nor flat. Either of these surfaces, or both, may be contoured. For example, if the contact surface has a convex contour, the effective length of the lever arm increases during rotation. However, in most applications this is not desired. In another alternative, the parallel slide surface is replaced by a flat but ramped surface 30 as shown in FIG. 2. In addition, in this figure the contact surface is replaced by a single contact point 32. This structure will result, prior to rotation, in an angular approach of the jaw finger to the component to be grasped. Rotation occurs in the same manner as previously described, with the contact point continuing to follow the ramp, but here adding to the downward displacement of the jaw finger. This particular configuration may be desired where increased displacement drawing a component to the base is required. Other contours can be used to arrive at different displacement cycles. Similarly, the effective length of the lever arm 2 and the jaw arm 8 can be altered to change the mechanical advantage of the device. However, there is an obvious tradeoff between mechanical advantage and displacement output of the finger 10. Typically, in a particular application, the restraints of the component size and overall tool dimensions will limit the useable dimensions of the jaw. What is necessary is that, at the time of rotation about the contact point, the contact point be sufficiently separated from the jaw finger in the direction orthogonol from the desired "down" or securing motion direction of the finger. This lateral separation will increase as the jaw slides along the slide surface. While the displacement of the jaw finger is referred to as sequential orthogonal motions, the angle of the slide surface, among other factors, may effect the actual motions. What is required to effect the proper action is at least two consecutive motions having at least component motions that are orthogonal. In this manner, locating and grasping of the appliance or component can be accomplished prior to completing the motion to secure the body to the impact base.

The jaw finger 10 is provided as one example of a means for capturing a component to the impact base. Many other alternative capture means are possible. One alternative is a "female" configured jaw arm. This entails a hole located in the jaw arm which is aligned with a mating pin on the component to be grasped. This type of feature would provide added lateral support. Other variations will be obvious to meet particular requirements. In applications such as described with prostheses, the invention may be used to withdraw as well as drive on the captured component. In such cases the finger element—and the entire jaw—must be sufficiently strong and rigid to accommodate the forces of withdrawal (such as applied by a slap-hammer).

A great advantage of the mechanical system taught here is the accommodation of various sizes. Because the orthogonal or downward motion of the finger restraining the component is initiated by contact with the component, variations in dimensions or sizes are automatically accommodated. Therefore if, during surgery to insert an implant, a change in size is required, the new trial piece or prosthesis is simply placed on the impact surface and the jaws retracted until the component is secured. No visual sizing of the tool to the new component is required. The user's hand grasping the tool handle need never be moved.

Figure 3:
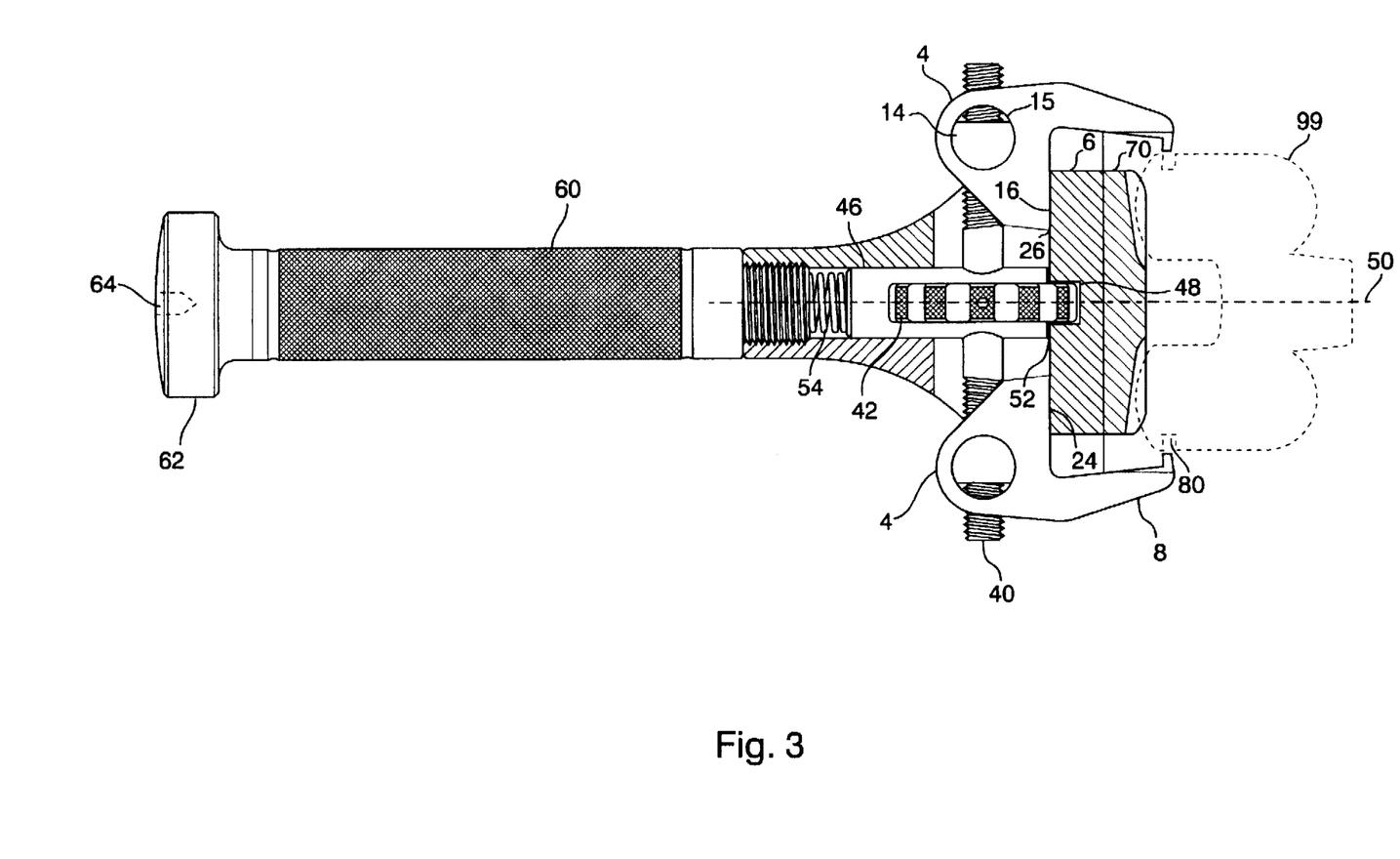
FIG. 3 is a section view of one embodiment of the invention having two jaws.
Figure 4:
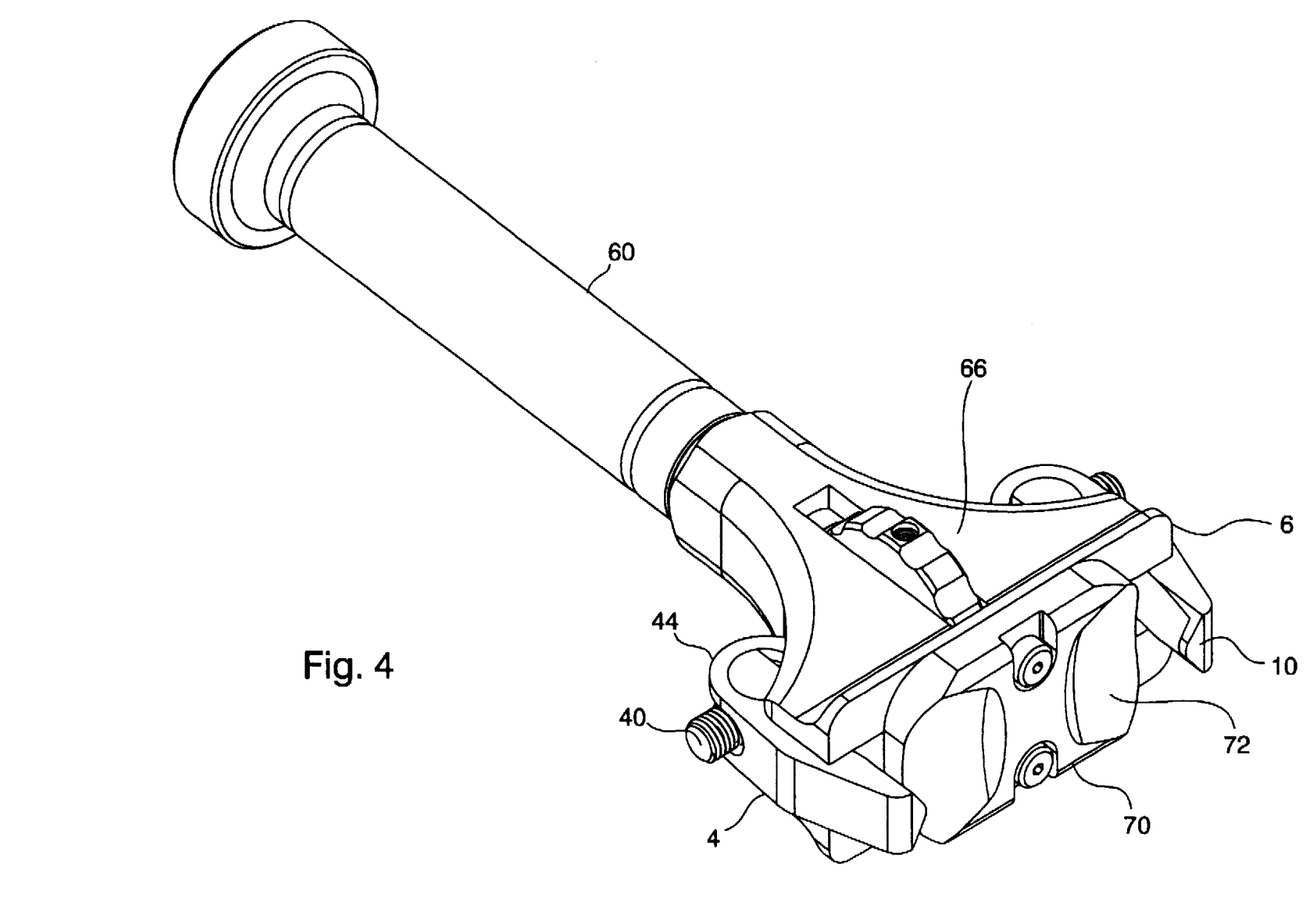
FIG. 4 is a perspective view of the embodiment of FIG. 3.

FIGS. 3 and 4 show the preferred embodiment of the invention. In this configuration two opposing jaws 4 are provided. Each has a pivot post 14 which resides in a loose sliding fit within a hole 15 bored through the respective jaw perpendicular to the plane of the jaw. In this embodiment, the retraction means is a rod 40 cut with left and right hand threads, respectively, on the opposing ends. The pivot posts 14 are both bored transversely and threaded to match the respective ends of the rod 40. The pivot posts are threaded symmetrically onto the rod ends thereby threadably capturing the jaws to the rod. To accommodate the rod, the jaws are slotted, resulting in the forming of two cheek flanges 44 through which the pivot posts 14 actually pass and reside. This slot must be deep enough to allow the jaws to rock on the pivot posts with enough play to allow rotation of the jaws when grasping a component. At the middle of the rod length, a thumb wheel 42 is secured via a set screw to the rod. The rod and thumb wheel are both captured in a transverse hole and slot, respectively, in a spring plunger 46. The fit of the hole and slot are such that the rod and thumbwheel can easily rotate relative to the spring plunger. One purpose of the spring plunger is to help control the location of the jaws. The thumbwheel extends beyond the spring plunger slot such as to enter a matching centering slot 48 in the impact base 6. The centering slot is cut centered on a centerline 50 of the impact base 6. When the jaws 4 are symmetrically threaded onto the rod 40 with respect to the thumbwheel 42 the centerline slot 48 acts as an aligning means to align the jaws symmetrically with respect to the impact base 6. Obviously, the thumbwheel could be offset from center and the centering slot equally so offset to effect the same result. In an alternative configuration, the thumbwheel is located to one side of the plunger 46. The plunger 46 extends beyond the rod 40 centerline to a plunger face end 52 which initially contacts the impact base 6. By making this face end 52 extend slightly beyond the plane of the jaw contact surfaces 24, the jaws are not forced against the impact base slide surface 16 and the pivot post threads are therefore initially unloaded allowing for easy operation of the thumbwheel. Otherwise the pressure of a plunger spring 54 which bears upon the opposite end of the plunger would translate into a load on the threads. This is distinct from the configuration shown in FIG. 1 where the arm remains in contact with the slide surface. The spring 54 is captured in a hole in a handle body 60 in which the plunger also is slidably deposited. By being compressed between the bottom of the hole and the plunger, the spring 54 biases the plunger toward the impact base and maintains the jaws in a ready position adjacent (rather than pressed against) the impact base. Note that in FIG. 3 the handle body 60 is shown in partial cutaway revealing that it is formed from two sections threaded together. This is principally for simplicity of manufacture and assembly. When formed in this way, it is preferred that the threaded joint bottom on a shoulder such that an impact load applied to the handle does not pass through a threaded section. A grip portion of the handle body is preferably elongated and of a size to comfortably fit a user's hand. The handle body lies generally along the centerline 50 of the impact base to provide a direct path for impact applied to the handle body end. The handle body 60 terminates at an enlarged knob 62 having a wide striking surface. At this end of the handle a threaded accessory connection 64 is formed centered in the striking surface for simple attachment of other devices such as a slap hammer. While the preferred handle body is as described above, where an application does not require impaction of the component, handles with other configurations can be used. For example, an angled handle or a pistol-grip type handle set perpendicular to the impact base centerline may be used. Any grip configuration should preferably provide close enough access to the actuator to allow single hand operation. The mechanism can also be structured without a handle. The impact base, jaws, retracting means and actuator may be integral with another tool or machine which does not utilize hand support. The function of the remaining elements remains the same and the single hand actuation advantage is still gained. As well, where a handle is not necessary, the actuation may be automated rather than manually performed.

From FIGS. 3 and 4 it can be seen that the impact base 6 is partially slotted at the ends to allow the jaws to traverse closer together. This allows the jaws to be positioned in a greater range accommodating a greater variation in size of components. Below the impact base, the tool is hollowed to form cheek plates 66 between which the threaded rod 40 is positioned and into which the jaws can be partially retracted. The cheeks cojoin again before necking down to the grip portion of the handle body 60. A capture plate 70 having sloped and cupped impaction surfaces 72 is also shown. The capture plate 70 is secured to the impact base by counter bored threaded fasteners. By using removable capture plates 70 of the appropriate shapes, the same tool can be easily altered to accommodate different component geometries. The surface can be shaped to match the component. In the device of FIG. 3 a double cupped shape accommodates the twin bulbs of a knee prosthesis 99 for the human femur. By using a properly sloped surface, the differing geometries of different sized components can be accounted for to bring each component into proper position on the impact base to be grasped by the jaw fingers. In a particular application, this slope will be determined by the particular components. A stepped capture plate could equally be used to accommodate various sizes. The capture plate may also allow use of softer materials to protect sensitive components or to introduce compressibility. Hard plastics, compatible with surgical devices, are preferred. The tool handle body and remaining elements are made of steel, preferably a stainless steel typical of that used for surgical tools and appliances.

Figure 5:
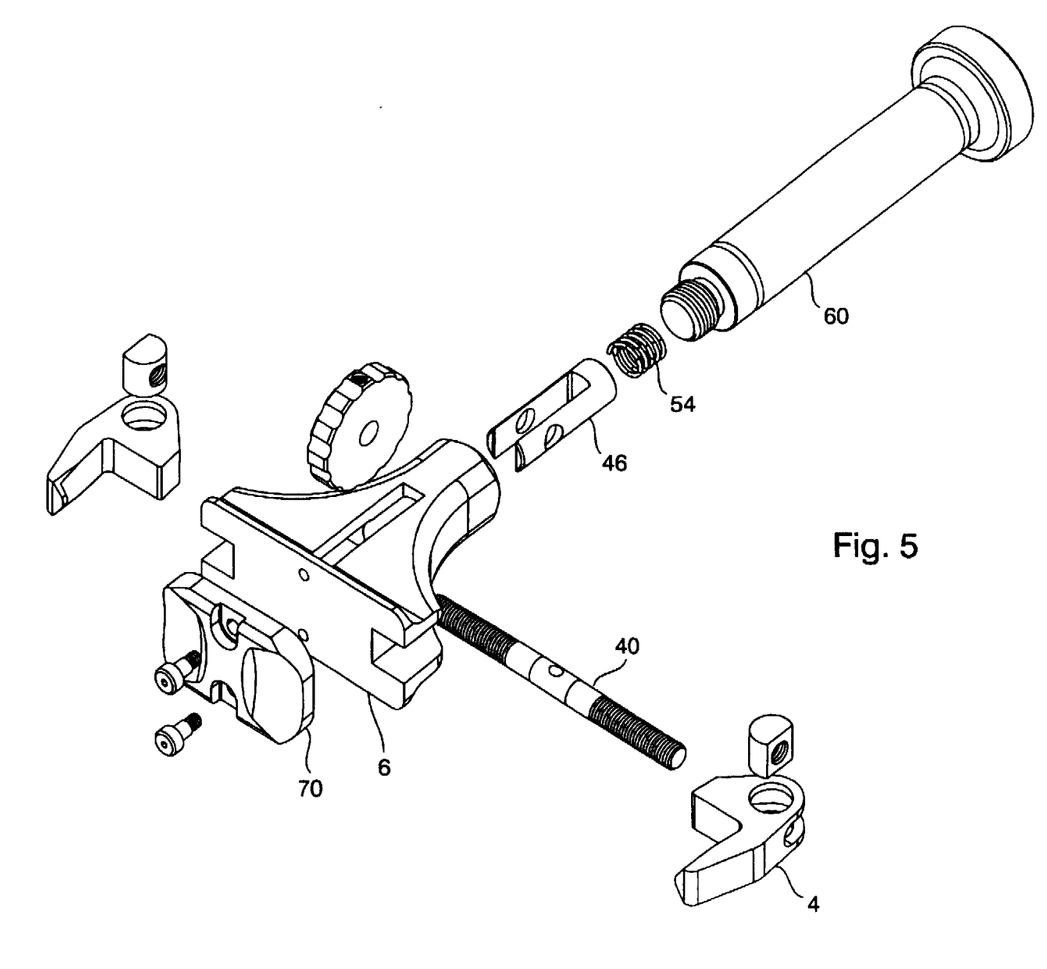
FIG. 5 is an exploded view of the embodiment of FIG. 3.

In FIG. 4, it can be seen that the jaw finger 10 is slightly pointed. In this case the component flange is matching with a v-shape. This shape provides a centering effect as the finger approaches and contacts the component. FIG. 5 is an exploded view of the same embodiment as in FIGS. 3 and 4. An additional advantage of the handle body being machined as two distinct parts can be seen in that the spring and plunger may be assembled from the back side of the spring bore prior to assembly of the handle.

The tool shown in FIGS. 3 and 4 operate in the same manner as previously described above. When the component is placed approximately centered in the capture plate 70, the thumbwheel 42 is turned by the thumb of the user's hand which is grasping the handle body 60. The jaws 4 are both drawn, together with the pivot posts, toward the impact base 6 centerline 50 by the threads on the rod 40 as it rotates with the thumbwheel. The wheel rotates easily at first as no load is on the system. The fingers 10 finally make contact substantially simultaneously with the component and are there stopped. The jaws rotate about the finger until their contact surfaces 24 make contact at the contact point 26 with the slide surface 16 of the impact base. The contact point is preferably slightly rounded. Until this moment the jaws have been essentially held off from the slide surface by the plunger 46. In the configuration shown, the slide surface is a single flat surface parallel to the rod centerline and perpendicular to the impact base centerline 50. As the thumbwheel is turned more and the pivot posts are retracted continually, the jaws rotate about the finger and the contact point forcing the jaws, rod, and plunger away from the impact base. The plunger spring 54 is compressed as the plunger is forced against it. As the jaws are forced downward, the fingers compress the component against the capture plate 70. To release the component, the thumbwheel is turned in the opposite direction. The hand gripping the handle need never be moved to effect the grasping and release motions. FIG. 3 shows a knee prosthesis component placed against the capture plate. The component ledge 80 by which the component will be grasped and drawn down by the finger 10 is shown.

The above examples are not intended to be limiting of the invention. It will be obvious to one skilled in the art to substitute equivalent mechanical elements for those described. In particular, the threaded rod, pivot posts and thumbwheel could be replaced as a retraction means by a lever type mechanism utilizing pinned links. Note that in the embodiment of FIG. 3 and 4 the threaded rod and thumbwheel are connected to the handle only through their capture in the moveable plunger. The jaws threaded on the rod ends are otherwise not restrained to the tool. Alternatively, the jaws could be linked to the impact base in a similar position. A lever type mechanism could then be easily employed to effect retraction and complete the system and tool. In another configuration, the jaws and finger face outward and driven apart rather than together to contact and grasp a component. In this case, two slide surfaces are provided against which the individual jaws rotate to draw down the respective fingers.

Figure 6:
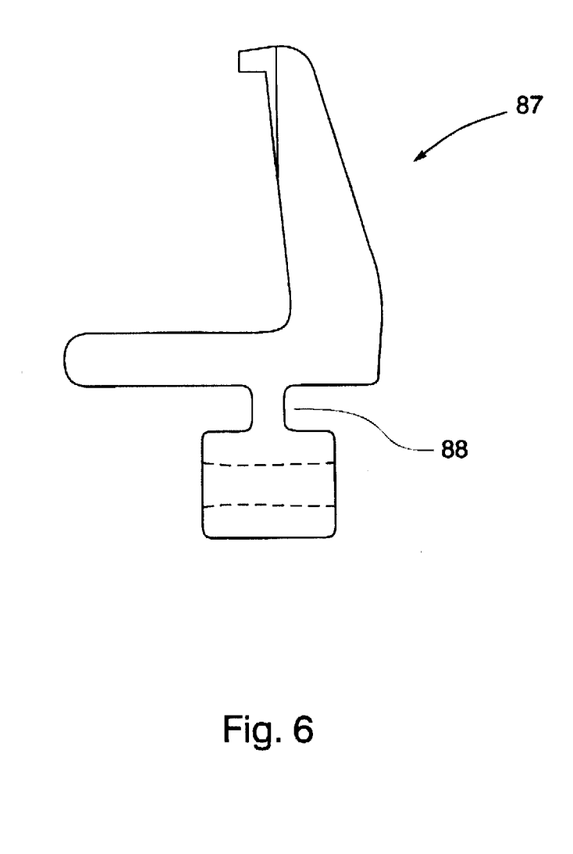
FIG. 6 shows an alternative jaw configuration.

Another alternative configuration, shown in FIG. 6, replaces the pivot post and pivot post hole with a necked-down region 88 formed in a resilient jaw 87. The retracting means is relatively rigidly connected to the jaw, rather than through a pivot. The jaw is at least partially formed of a resilient material such as a tough plastic. A necked-down region of reduced cross section is formed in the jaw between the retracting means connection and the arms of the jaw. This necked-down region allows the jaw arms to rotate relative to the retracting means resulting in the same desired motion. The pivot axis effectively being within and passing through the necked down region.

I claim:

1. A tool providing for one-handed grasping and securing of a component onto a handle, the tool comprising:
   a. a handle,
   b. an impact base, said base having at least one slide surface, and said base being integral with said handle,
   c. at least one jaw, each jaw having a pivot axis, a lever arm extending perpendicularly outward from said pivot axis, said lever arm having a contact point located adjacent to said slide surface, and each jaw having a jaw arm extending perpendicularly outward from said pivot axis, said jaw arm terminating in a capture means,
   d. means for retracting said jaws, said retracting means being pivotly connected to each of said jaws at said pivot axis, and said retracting means being moveably connected to said handle,
   e. an actuator connected to said retracting means, whereby with a single continued movement of the actuator each of the jaws are moved in a first direction to contact and grasp an external component and are subsequently moved in a second direction to draw the component into a secure position against the impact base.

2. The tool according to claim 1 wherein:
   a. said at least one jaw comprises a first and second jaw,
   b. said retracting means comprises: an elongated rod having a first and second end, said first and second end being threaded in respectively opposite directions, a first and second pivot post, said first pivot post having internal threads matching said first said rod end and being disposed thereon and said second pivot post having internal threads matching said second rod end and being disposed thereon, said first and second pivot post being pivotably connected respectively to said first and second jaw at the respective said pivot axis, such that a single continued movement of the actuator imparts a rotational movement to said rod thereby drawing the jaws together in a first direction on the rod until said capture means contact the component to be grasped, whereby each of the jaw capture means is forced in a direction at least in part orthogonal to said first direction thereby forcing said capture means to grasp and secure the component against said impact base.

3. The tool according to claim 2 wherein:
   said actuator is a thumbwheel secured to said rod, and
   each said capture means comprises a finger extending laterally from said jaw arm.

4. The tool according to claim 3, further comprising:
   a biasing means for biasing said retracting means toward said impact base such that said contact surfaces are held in proximity of said slide surfaces.

5. The tool according to claim 4, wherein
   said handle has a longitudinal bore; and
   said biasing means comprises:
      a plunger, said plunger being partially and moveably disposed within said bore and said plunger having a transverse hole and having a terminal end, said terminal end being located generally on a plane with said contact surfaces, said rod being rotatably disposed in said hole; and a spring disposed within said bore and terminating against said plunger and biasing said plunger terminal end against said impact base.

6. The tool according to claim 5, further comprising:

an aligning means for aligning said retracting means and said jaws symmetrically with respect to said impact base.

7. The tool according to claim 6, wherein:

said aligning means is a slot located along a center line of said impact base, said thumbwheel being partially disposed within said slot, such that said thumbwheel is substantially restrained from lateral motion while allowing rotational motion of said thumbwheel and threaded rod.

8. The tool according to claim 4, further comprising:

a component capture plate, said capture plate being secured to said impact base.

9. The tool according to claim 8, wherein:

said capture plate is formed of a hard plastic.

10. The tool according to claim 9, wherein:

said capture plate has a contoured surface for receiving components to be grasped.

11. A tool providing for one-handed grasping and securing of a component onto a handle, the tool comprising:

a. an elongated handle;

b. an impact base, said impact base having an impact surface and having at least one slide surface, and said impact base being rigidly connected to said handle;

c. a first and second jaw, both of said jaws having
a pivot axis, a lever arm extending outward from said axis, said lever arm having a contact point, and each jaw having a jaw arm extending outward from said pivot axis, said jaw arm terminating in a finger;

d. a retractor, said retractor being moveably connected to said handle, and said retractor comprising:
a elongated rod, said rod having a first and second end, said first and second end being threaded in respectively opposite directions; and said elongated rod being threadably connected to said first jaw at said first end and to said second jaw at said second end;

e. an actuator connected to said retractor;
said first and second jaw being oriented on said rod, and said rod being oriented such that both of said jaw arms terminate adjacent said impact surface while both of said contact points are held adjacent to said at least one slide surface;

whereby with a single continued movement of the actuator, both of the fingers are moved in a first direction generally parallel with said impact face and, subsequent to interference of this motion by an external component contact with said fingers, are then moved in a second direction more toward the impact face.

12. A tool according to claim 11, wherein: each said jaw further comprises a necked down region formed of a resilient material, said necked down region interposed between said arms and said rod, and said necked down region functionally defining said pivot axis.

13. A tool providing for one-handed grasping and securing of a component, the tool comprising:

a. an impact base, said base having at least one slide surface, b. at least two jaws, each jaw having
a pivot axis, a lever arm extending perpendicularly outward from said pivot axis, said lever arm having a contact point located adjacent to said slide surface, and each jaw having a jaw arm extending perpendicularly outward from said pivot axis, said jaw arm terminating in a capture means, c. means for retracting said jaws, said retracting means being pivotly connected to each of said jaws at said pivot axis, d. an actuator connected to said retracting means,
whereby with a single continued movement of the actuator each of the jaws are moved in a first direction to contact and grasp an external component and are subsequently moved in a second direction to draw the component into a secure position against the impact base.

* * * * *